United States Patent
Walker et al.

(10) Patent No.: US 10,192,031 B1
(45) Date of Patent: Jan. 29, 2019

(54) SYSTEM FOR EXTRACTING INFORMATION FROM DICOM STRUCTURED REPORTS

(71) Applicant: VIDISTAR, LLC, Greenville, SC (US)

(72) Inventors: Craig A. Walker, Greenville, SC (US); Michal Kostrzewa, Warsaw (PL)

(73) Assignee: VIDISTAR, LLC, Greenville, SC (US)

( * ) Notice: Subject to any disclaimer, the term of this patent is extended or adjusted under 35 U.S.C. 154(b) by 533 days.

(21) Appl. No.: 14/941,467

(22) Filed: Nov. 13, 2015

Related U.S. Application Data

(63) Continuation-in-part of application No. 13/507,195, filed on Jun. 11, 2012, which is a continuation-in-part of application No. 12/932,973, filed on Mar. 10, 2011, now Pat. No. 8,200,505, which is a continuation of application No. 11/592,608, filed on Nov. 3, 2006.

(51) Int. Cl.
G06F 19/00 (2018.01)
G16H 50/70 (2018.01)

(52) U.S. Cl.
CPC .......... *G06F 19/321* (2013.01); *G16H 50/70* (2018.01)

(58) Field of Classification Search
CPC ... G06F 17/2247; G06F 17/227; G06F 19/321
See application file for complete search history.

(56) References Cited

U.S. PATENT DOCUMENTS

| | | | |
|---|---|---|---|
| 6,643,641 | B1 | 11/2003 | Snyder |
| 7,283,857 | B1 | 10/2007 | Fallon et al. |
| 2002/0143727 | A1 | 10/2002 | Hu et al. |
| 2003/0187689 | A1 | 10/2003 | Barnes et al. |
| 2004/0083217 | A1 | 4/2004 | Brackett et al. |
| 2004/0122844 | A1 | 6/2004 | Malloy et al. |
| 2004/0165700 | A1 | 8/2004 | Batchelder et al. |
| 2004/0252871 | A1 | 12/2004 | Tecotzky et al. |
| 2005/0149536 | A1 | 7/2005 | Wildes et al. |
| 2005/0273365 | A1 | 12/2005 | Baumgartner et al. |
| 2006/0004745 | A1 | 1/2006 | Kuhn et al. |
| 2006/0282447 | A1 | 12/2006 | Hollebeek |
| 2006/0285753 | A1 | 12/2006 | Yamasaki |
| 2007/0025606 | A1 | 2/2007 | Gholap et al. |
| 2007/0078674 | A1 | 4/2007 | Weinberg et al. |
| 2008/0109250 | A1 | 5/2008 | Walker et al. |
| 2009/0164474 | A1 | 6/2009 | Noumeir |
| 2009/0177637 | A1 | 7/2009 | Hollebeek |
| 2010/0008553 | A1 | 1/2010 | Holmstrom |

(Continued)

OTHER PUBLICATIONS

Sereboff, "Non-final Office Action dated Feb. 19, 2016", U.S. Appl. No. 14/081,054, The United States Patent and Trademark Office, Feb. 19, 2016.

(Continued)

*Primary Examiner* — Neal Sereboff
(74) *Attorney, Agent, or Firm* — Lindauer Law, PLLC

(57) ABSTRACT

Described are techniques for extracting information from DICOM structured reports by applying criteria to the reports to locate values at particular nodes and extract the values into a data structure. One or more rules may be applied to determine additional values based on the extracted values. One or more of the extracted values or additional values may be queried, indexed, aggregated, and stored for searching, access, report generation, and so forth.

20 Claims, 6 Drawing Sheets

(56) References Cited

U.S. PATENT DOCUMENTS

2011/0129131 A1 6/2011 Avinash et al.
2012/0323118 A1 12/2012 Menon Gopalakrishna et al.

OTHER PUBLICATIONS

"Digital Imaging and Communications in Medicine (DICOM) Part 20: Transformation of DICOM to and from HL7 Standards", National Electrical Manufacturers Association, PS. Mar. 20, 2011, 2011, pp. 1-78.

HTTP Definition as downloaded from rhyshaden.com Feb. 2005 version of page.

"Introduction to Networking and the OSI Model", Pearson. Ch. 1, Jan. 3, 2001, pp. 1-22.

Sun Microsystems, Inc., "JAVA™ Web Start Overview", White Paper, May 2005.

Oracle, "Oracle9i Reports, Building Reports Release 9.0", Part No. B10310-01, Oct. 2002.

VidiStar, "Presenting . . . VidiStar's Standalone Viewer™", 2004.

Clunie, David A., "Medical Image Format FAQ", Mar. 12, 2006.

Hussein, et al., "DICOM Structured Reporting Part 2. Problems and Challenges in Implementation for PACS Workstations", infoRAD, vol. 24, No. 3, RSNA, 2004, pp. 897-909.

Kalet, et al., "A declarative implementation of the DICOM-3 network protocol", Journal of Biomedical Informatics 36 (2003) pp. 159-176. Received Feb. 21, 2003.

Mhiri, et al., "An Ontology Visualization Tool for Indexing DICOM Structured Reporting (SR) Documents", CRIP5, University of Paris V, 75006 Pads, France.

Mhiri, et al., "Ontology Usability Via a Visualization Tool for the Semantic Indexing of Medical Reports (DICOM SR)", A. Holzinger (Ed.): USAB 2007, LNCS 4799, pp. 409-410, 2007.

Noumeir, Rita, "Benefits of the DICOM Structured Report", Journal of Digital Imaging, vol. 19, No. 4 Dec. 2006: pp. 295-306.

Sereboff, Neal, "Notice of Allowance dated Mar. 23, 2012", U.S. Appl. No. 12/932,973, The United States Patent and Trademark Office, Mar. 23, 2012.

Sereboff, Neal, "Final Office Action dated Jul. 13, 2015", U.S. Appl. No. 13/507,195, The United States Patent and Trademark Office, Jul. 13, 2015.

Sereboff, Neal, "Non-Final Office Action dated Mar. 19, 2015", U.S. Appl. No. 13/507,195, The United States Patent and Trademark Office, Mar. 19, 2015.

Sereboff, Neal, "Final Office Action dated Nov. 10, 2010", U.S. Appl. No. 11/592,608, The United States Patent and Trademark Office, Nov. 10, 2010.

Sereboff, Neal, "Non-Final Office Action dated Apr. 21, 2010", U.S. Appl. No. 11/592,608, The United States Patent and Trademark Office, Apr. 21, 2010.

Sereboff, Neal, "Non-Final Office Action dated Nov. 25, 2011", U.S. Appl. No. 12/932,973, The United States Patent and Trademark Office, Nov. 25, 2011.

Tachibana, et al., "Design and Development of a Secure DICOM-Network Attached Server". Originally published in Jpn J Radiol Technol, 62(4), (2006), 529-538.

Toffoli, Giulio, "iReport User Manual, version 1.0", copyright 2004.

Walker, Craig A., "VidiStar, LLC Receives the 2013 InnoVision Award for Technology Development", VidiStar LLC—DICOM PACS Online Medical Imaging Software, Nov. 8, 2013. [retrieved on Aug. 18, 2015]. Retrieved from the Internet: <http://www.vidistar.com/vidistar-llc-receives-the-2013-innovision-award-for-technology-development>.

SYSTEM FOR EXTRACTING INFORMATION FROM DICOM STRUCTURED REPORTS

CROSS-REFERENCE TO RELATED APPLICATIONS

The present application is a continuation-in-part of and claims priority to the pending U.S. patent application Ser. No. 13/507,195, filed on Jun. 11, 2012, entitled "Systems and Methods for Data Mining of DICOM Structured Reports". U.S. patent application Ser. No. 13/507,195 in turn claims priority to U.S. patent application Ser. No. 12/932,973, filed on Mar. 10, 2011, now U.S. Pat. No. 8,200,505, entitled "System and Method for Creating and Rendering DICOM Structured Clinical Reporting via the Internet". U.S. patent application Ser. No. 12/932,973 in turn is a continuation application that claims priority to U.S. patent application Ser. No. 11/592,608, filed Nov. 3, 2006, now abandoned. U.S. patent application Ser. Nos. 13/507,195; 12/932,973; and 11/592,608 are incorporated by reference herein in their entirety.

BACKGROUND

Many medical images and related reports are standardized using the Digital Imaging and Communications in Medicine (DICOM) standard. DICOM Structured Reports (DSR) are often stored in a Picture Archiving and Communications System (PACS) or a similar repository in a format that may not be directly queried for information.

BRIEF DESCRIPTION OF FIGURES

The detailed description is set forth with reference to the accompanying figures. In the figures, the left-most digit(s) of a reference number identifies the figure in which the reference number first appears. The use of the same reference numbers in different figures indicates similar or identical items or features.

Figure 1:
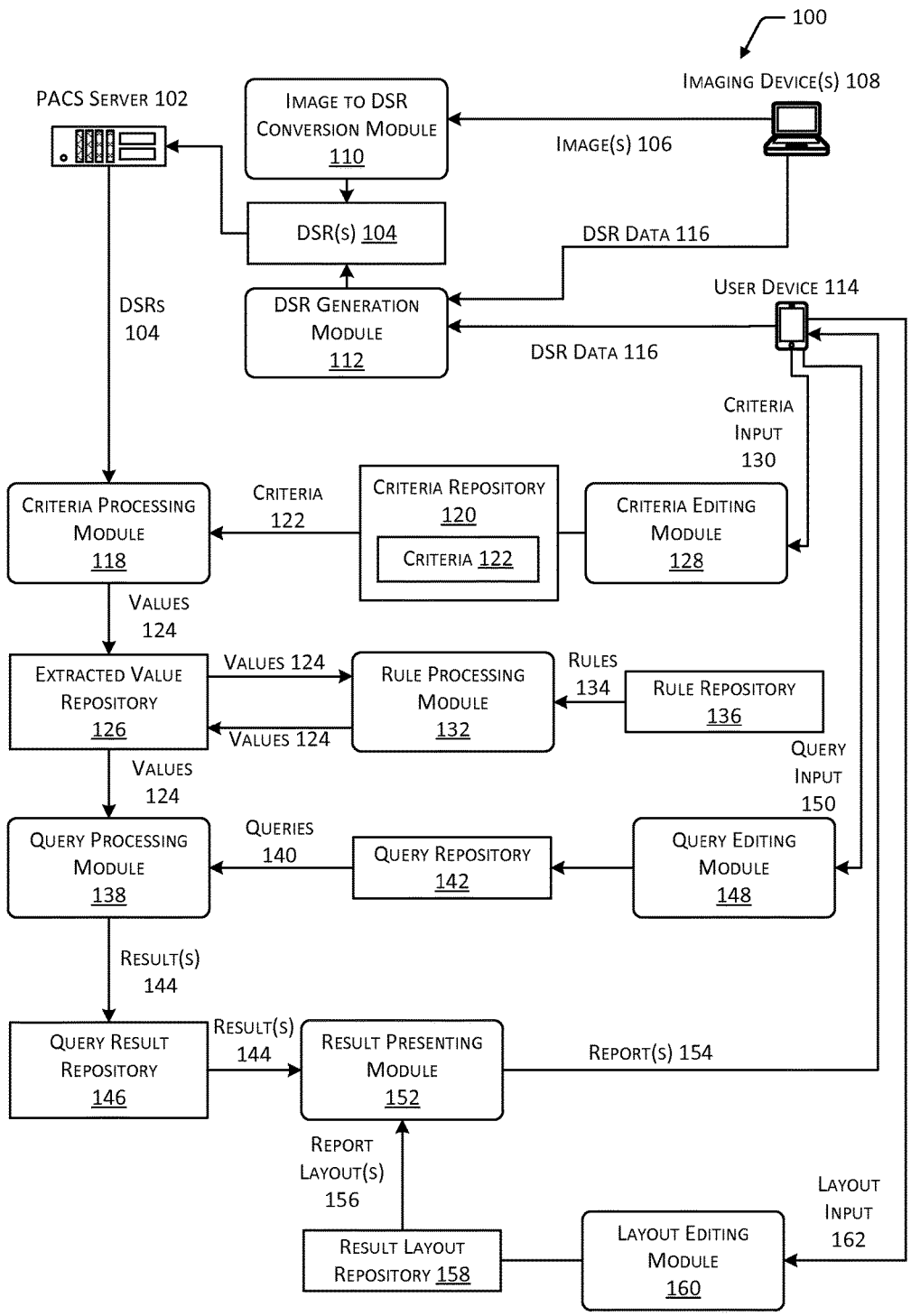
FIG. 1 depicts a system for extracting values from DSRs, generating additional values based on the extracted values, and generating a report based on one or more queries.

While implementations are described in this disclosure by way of example, those skilled in the art will recognize that the implementations are not limited to the examples or figures described. It should be understood that the figures and detailed description thereto are not intended to limit implementations to the particular form disclosed but, on the contrary, the intention is to cover all modifications, equivalents, and alternatives falling within the spirit and scope as defined by the appended claims. The headings used in this disclosure are for organizational purposes only and are not meant to be used to limit the scope of the description or the claims. As used throughout this application, the word "may" is used in a permissive sense (i.e., meaning having the potential to) rather than the mandatory sense (i.e., meaning must). Similarly, the words "include", "including", and "includes" mean "including, but not limited to".

DETAILED DESCRIPTION

The DICOM standards, published by the National Electronic Manufacturers Association (NEMA), outline a desired data format, flow, and hierarchy of electronic information in diagnostic images to facilitate the transfer of information between computer systems. However, many existing medical devices provide images and other output in proprietary, unstructured formats that may vary depending on the type of device, the manufacturer of the device, the model of the device, and so forth. For example, output produced by a medical device may include images, text, or both images and text, having fonts, formats, layouts, and so forth, specific to a particular modality of the device. Often, the data output by a medical device is not readily machine-readable. U.S. patent application Ser. Nos. 13/507,195; 12/932,973; and 11/592,608 describe systems and methods that may be used to extract data from these and other types of output to produce standardized DSRs.

Information found in DSRs may be of use to physicians, patients, pharmaceutical companies, and other users. Additionally, information stored in DSRs may be further stored, transmitted, or manipulated for use or processing by other software. However, because a DSR typically includes image files stored in a PACS server or similar type of repository, DSRs may not readily be queried for information using conventional reporting and data mining tools (e.g., On-Line Analytical Processing (OLAP) tools).

This disclosure relates to systems and methods for performing data mining, querying, and other operations relating to DSRs. A DSR may include a tree structure having one or more nodes, at least a portion of the nodes containing a value. For example, a node of a DSR may include a container, a field associated with alphanumeric data, spatial or temporal coordinates, a reference to an image, and so forth. Nodes may also include references to other nodes. For example, the value in a first node may be dependent upon the value(s) present in one or more other nodes. The standardized structure of DSRs is more thoroughly described in "The DICOM Standard 2015", managed by the Medical Imaging & Technology Alliance (a division of NEMA), which is incorporated by reference herein.

To determine information from one or multiple DSRs, one or more criteria for extracting values from nodes may be accessed, received, or generated based on user input. A criterion may include one or more structured report paths used to access one or more particular nodes within a DSR. A structured report path may include code or logic indicative of the location of a particular node in a DSR. For example, a criterion may be configured to determine the value for an ejection fraction from a DSR related to a cardiology study. A structured report path of the criterion may be configured to locate a container node within a DSR having the identifier "DCM/121070/Findings", which would include medical findings. While multiple DSRs may have such a container node, the criterion may be configured to locate only those container nodes having an associated concept modifier node with the identifier "SRT/G-C171/Laterality" and the value "SRT/G-A100/Right". In such a container node, the structured report path may then be used to locate a numeric node having the identifier "DCM/122211/Left Ventricular Ejection Fraction", which may contain a desired value to be extracted by the criterion. In some implementations, a criterion may be configured to locate multiple nodes. For example, a structured report path of a criterion may be configured to locate a container node associated with the identifier "DCM/121109/Indications for Procedure", and to extract the values from all child nodes that depend from the located container node.

In some implementations, a criterion may be configured to manipulate or process values extracted from a DSR. A criterion may be configured to individually store node values as a "collection type", to aggregate multiple values, to normalize extracted values to certain units of measurement, to store one or more particular values, and so forth. For example, a criterion may be configured to locate all numeric nodes having the identifier "LN/11726-7/Peak Velocity", extract the value from each of these nodes, and normalize the values to a particular unit of measurement, such as centimeters per second (cm/s). Continuing the example, the criterion may be configured to store (e.g., in a data structure) the maximum value located through this process as the maximum peak velocity for a study.

In some implementations, a criterion may be generated based on user input. For example, a graphical user interface (GUI) may be presented to a user device, the GUI including fields, selectable elements, and so forth, that may be used to input or select particular medical findings, medical impressions, and so forth. Each field or selectable element may be mapped to one or more structured report paths. The resulting criterion may be configured to extract values from nodes in one or more DSRs corresponding to the structured report path(s). In other implementations, an existing, stored criterion may be accessed or a criterion may be received from a user device or other source. For example, a user may input a structured report path, one or more extraction instructions for processing or manipulating a value, and so forth, to generate a criterion, and provide the generated criterion for use. As another example, a user may provide input indicative of a preexisting, previously received, or previously stored criterion.

The particular DSRs to be processed may be determined based on one or more of user input or the criteria. For example, a criterion may indicate one or more particular DSRs or a characteristic associated with one or more DSRs. Continuing the example, each DSR having a title, node, identifier, or other characteristic that corresponds to a criterion may be processed using the criteria to determine values associated with one or more nodes. In some implementations, correspondence between the structured report path of a criterion and one or more DSRs may be determined. DSRs that have a node corresponding to the structured report path may be suitable for analysis using the criterion. In other implementations, one or more criteria may be used to determine values from a particular DSR or group of DSRs based on user input selecting particular DSRs for analysis or particular criteria for application. In some implementations, a criterion may be automatically or manually applied to new or modified DSRs. For example, if a new DSR is received and stored in a report repository or if an existing DSR is modified, one or more criteria that correspond to the received or modified DSR may be used to extract values from the DSR.

Values extracted from DSRs by criteria may be stored in various types of data structures, such as tables, databases, and so forth. For example, extracted values may be stored in a table in which columns correspond to particular fields of a DSR, rows correspond to particular DSRs, and individual cells contain values from particular DSRs for particular fields. In some implementations, extracted values may be associated with a study from which one or more DSRs were determined, rather than to a DSR, itself. For example, a study may include multiple DSRs, such as a preliminary DSR, created by a machine, that includes initial information from a sonographer, a final DSRs created by a physician that may include amendments to the sonographer's impressions, and any number of additional DSRs. By associating extracted values with a study, a query may be used to answer questions such as "what was the Ejection Fraction of the left Ventricle of this study" rather than querying individual DSRs. Additionally, by associating extracted values with a study, a single criterion may be used to determine different information from different DSRs. For example, a criterion may be configured to determine a date at which a DSR was signed. When processing a primary DSR, the criterion may determine the date on which the sonographer signed the preliminary DSR. When processing the final DSR, the criterion may determine a later date on which the physician signed the final DSR. These determined values may be associated with a study as two separate attributes. For example, a table associated with the study may include two columns: a first indicating when the study was read by a sonographer and a second indicating when the study was read by a physician.

In some implementations, the values extracted from DSRs may be used to determine and store additional values in a data structure. For example, one or more rules, scripts, and so forth, may be applied to extracted values to determine subsequent values that depend from the extracted values. Continuing the example, a rule may determine whether a particular value for a dimension of a vascular structure is greater or less than 3 centimeters (cm). An indication of this determination (e.g., true, false, >3 cm, <3 cm, and so forth) may be stored in association with other extracted values. For example, a table of extracted values may include an additional column containing an indication whether the determined dimension exceeds 3 cm, even though the DSRs used to generate the table do not include a specific indication of this fact. As another example, a rule may determine whether multiple extracted values indicate a medical condition, such as heart disease. Continuing the example, the rule may determine whether multiple values and particular combinations of values fall within or outside of particular ranges. A rule may include any number of variables or formulae and may produce one or multiple outputs. In some implementations, a rule may include an indication of a particular type of report for which the rule is to be used.

Extracted values may be queried using OLAP reporting tools or other types of querying or reporting tools that may be used to build queries, pivot tables, reports, and so forth. For example, user input indicative of one or more DSRs, criteria, or values may be received, and values that correspond to the user input may be determined for inclusion in a response to a query generated by a user. In some implementations, user input indicative of one or more report layouts or templates may be received, and the report layout or template may be populated with data corresponding to a response to the query. For example, a third party reporting tool, such as those produced by Pentaho of Orlando, Fla., MicroStrategy, Inc. of Tysons Corner, Va., Tableau Software of Seattle, Wash., or Oracle Corporation of Redwood City, Calif., may be used to generate reports based on query results.

FIG. 1 depicts a system 100 for extracting values from DSRs, generating additional values based on the extracted values, and generating a report based on one or more queries. A PACS server 102 or another type of computing device or storage medium may be used to store one or more DSRs 104 obtained from various modalities. For example, images 106 or other types of data generated by imaging devices 108 or other types of medical equipment may be provided (e.g., via one or more networks) to an image to DSR conversion module 110 associated with the PACS server 102. The image to DSR conversion module 110 may generate DSRs 104 automatically (e.g., responsive to receipt of images 106 or other data) or manually (e.g., responsive to user input). Possible image to DSR conversion modules 110 are described in U.S. patent application Ser. Nos. 13/507,195; 12/932,973; and Ser. No. 11/592,608. In cases where data generated by the imaging device 108 is machine-readable without conversion, use of the image to DSR conversion module 110 may be omitted. In other implementations, one or more DSRs 104 may be generated via user input using a DSR generation module 112. For example, a user associated with a user device 114 may provide DSR data 116, such as images 106, text, and so forth, to the PACS server 102. In other implementations, an imaging device 108 may generate DSR data 116 that is machine-readable without processing using the image to DSR conversion module 110. The DSR generation module 112 may be used to generate one or more DSRs 104 based on the DSR data 116. In other implementations, the DSR generation module 112 may be associated with the user device 114, the imaging device 108, or another device remote from the PACS server 102, and the DSR 104 generated by the DSR generation module 112 may be provided to the PACS server 102.

A criteria processing module 118 in communication with the PACS server 102 may request or access one or more of the DSRs 104 stored in association with the PACS server 102 to extract information therefrom. Specifically, the criteria processing module 118 may communicate with a criteria repository 120 containing one or more criteria 122. The criteria processing module 118 may determine correspondence between one or more of the criteria 122 and one or more of the DSRs 104 to determine particular criteria 122 to be applied to particular DSRs 104. For example, a criterion 122 may include a structured report path or another type of indication or identifier corresponding to a particular type of DSR 104, a particular node or type of node within a DSR 104, a particular value or type of value in a DSR 104, and so forth. Based on correspondence between the criterion 122 and one or more of the DSRs 104 associated with the PACS server 102, a subset of the DSRs 104 that are suitable for application of the criterion 122 may be determined. For example, a criterion 122 having a structured report path corresponding to a particular type of node may correspond to a DSR 104 having such a node. DSRs 104 that lack a corresponding node may not be suitable for analysis using the criterion 122 (e.g., an attempt to extract a value 124 from a DSR 104 lacking a corresponding node may fail or yield a null result). After determining a subset of corresponding DSRs 104, the structured report path of the criterion 122 may be used to locate one or more particular nodes within the subset of DSRs 104 from which values 124 may be extracted using the criterion 122. Extracted values 124 may be stored in an extracted value repository 126, which may include any manner of database, table, or other data structure contained within a computer-readable storage medium (CRSM).

In some implementations, a criterion 122 may include extraction instructions, the extraction instructions indicating a process by which particular values 124 may be extracted from associated nodes in a DSR 104. In some cases, the extraction instructions may be relatively simple. For example, the extraction instructions may be configured to determine a numerical value within a node and write that numerical value to a designated location in a table stored in the extracted value repository 126. In other cases, the extraction instructions may require analyses of images 106, dependences between nodes, and so forth. The extraction instructions may also be configured to process or manipulate an extracted value 124. For example, the extraction instructions may convert the extracted value 124 to a particular unit of measurement, such that a set of corresponding values 124 stored in the extracted value repository 126 share a common unit of measurement.

In some implementations, the criteria processing module 118 may maintain the integrity of the extracted value repository 126 and ensure that the information therein remains current by accounting for one or more of: the addition of new criteria 122 to the criteria repository 120, the modification of one or more criteria 122 in the criteria repository 120, the addition of new DSRs 104 to the PACs server 102, or the modification of one or more of the DSRs 104 in the PACS server 102. For example, if a new criterion 122 is added to the criteria repository 120 or an existing criterion 122 is modified, the criteria processing module 118 may apply the new or modified criterion 122 to one or more DSRs 104. In some implementations, the criteria processing module 118 may apply the new or modified criterion 122 to all studies (and associated DSRs 104) stored in the PACS server 102. In many cases, the addition or modification of a criterion 122 may cause the addition of columns to a table associated with one or more studies. Processing of all of the studies using the new or modified criterion 122 may populate values for the added columns. The resulting extracted values 124 may replace existing values 124 in the extracted value repository 126, or the resulting values 124 may be added to the extracted value repository 126 as new values 124. In some implementations, if a new or modified criterion 122 results in a modification to a DSR 104 or associated data, the criterion 122 may cause a copy of the DSR 104 to be generated, the copy of the DSR 104 including one or more modifications. A copy of a DSR 104 may include one or more references to the preceding DSR 104 from which it was copied. In other implementations, correspondence between the structured report path of the new or modified criterion 122 and one or more of the DSRs 104 may be used to determine a subset of DSRs 104 to which the criterion 122 may be applied. As another example, if a new DSR 104 is added to the PACS server 102 or if an existing DSR 104 is modified, the criteria processing module 118 may apply one or more criteria 122 to the new or modified DSR 104. The resulting extracted values 124 may replace existing values 124 in the extracted value repository 126, or the resulting values 124 may be added to the extracted value repository 126 as new values 124. In some implementations, all of the criteria 122 may be applied to the new or modified DSR 104. In other implementations, correspondence between the structured report path of the criteria 122 and the new or modified DSR 104 may be used to determine a subset of the criteria 122 to be applied to the DSR 104.

A criteria editing module 128 may also be in communication with the criteria repository 120. The criteria editing module 128 may be used to create or modify criteria 122 based on user input from one or more user devices. For example, the criteria editing module 128 may provide a GUI to a user device 114. The GUI may include fields, selectable elements, and so forth, that may be used to input or select particular medical findings, impressions, and so forth. Each field or selectable element may be mapped to a particular structured report path. The criteria editing module 128 may generate or modify one or more criteria 122 based on criteria input 130 (e.g., user input) selecting particular elements or completing particular fields. In other implementations, criteria input 130 received from a user device 114 may include structured report paths, indications of report or value types, extraction instructions, and so forth, which may be used to generate or modify one or more criteria 122.

In some implementations, a rule processing module 132 may access one or more rules 134 stored in a rule repository 136 for application to one or more extracted values 124. While FIG. 1 depicts the rule processing module 132 and criteria processing module 118 as separate modules and the rules 134 and criteria 122 as separate data, in some implementations, the rules 134 may be a part of the criteria 122. For example, a criterion 122 may be provided with a rule 134, script, or other type of code or instructions configured to manipulate an extracted value 124 or to determine additional values 124 based on one or more extracted values 124. The criteria processing module 118 may therefore include a rule processing module 132 configured to apply the rules 134 to the extracted values 124.

A rule 134 may include an indication of one or more values 124 or types of values 124 to which the rule 134 is to be applied. The rule 134 may also include instructions for modifying existing values 124 or generating additional values 124 based on the outcome of the rule 134. As such, the rule processing module 132 may receive current values 124 from the extracted value repository 126 as inputs and provide modified or additional values 124 to the extracted value repository 126 as outputs. For example, a rule 134 may be configured to determine whether a particular numerical value 124 or set of values 124 exceeds a threshold number. Responsive to this determination, the rule 134 may modify each value 124 that does not exceed the threshold number by setting the value to zero. As another example, responsive to the determination whether a value 124 exceeds a threshold, the rule 134 may generate a new value 124 for each DSR 104 having an identifier "N>threshold" and a Boolean value of "true" or "false" based on whether the value 124 exceeds the threshold. As yet another example, a rule 134 may be configured to identify the greatest extracted value 124 from a group of multiple extracted values 124 of the same type. As another example, a rule 134 may be configured to determine relationships between multiple values 124 and multiple thresholds. Continuing the example, a particular set of relationships between values 124 and thresholds may indicate a particular medical condition. Based on the outcome of application of the rule 134, the rule 134 may generate a new value 124 indicating the presence or absence of the particular medical condition. In some implementations, rules 134 in the rule repository 136 may be modified, new rules 134 may be added, or existing rules 134 may be removed based on user input. For example, criteria input 130 to modify or create one or more criteria 122 may include input creating or modifying one or more rules 134.

A query processing module 138 in communication with the extracted value repository 126 may be used to aggregate or report information from the extracted value repository 126. Specifically, the query processing module 138 may access one or more queries 140 from a query repository 142 for application to values 124 stored in the extracted value repository 126. A query 140 may include one or more values 124, indications of particular types or categories or identifiers of values 124, threshold numbers, and so forth. For example, a query 140 may be used to filter or aggregate particular DSRs 104 based on the presence or absence of particular values 124 in the DSRs 104, the relationship between particular values 124, the relationship between values 124 and one or more thresholds, and so forth. The outcomes of the queries 140 (e.g., result datasets) may be stored as results 144 in a query result repository 146.

In some implementations, the query processing module 138 may ensure that the information in the query result repository 146 remains current by accounting for one or more of: the addition of new queries 140 to the query repository 142, the modification of existing queries 140 in the query repository 142, the addition of new values 124 in the extracted value repository 126, or the modification of existing values 124 in the extracted value repository 126. For example, if a new query 140 is added or an existing query 140 is changed, the query processing module 138 may apply the new or modified query 140 to at least a subset of the values 124 in the extracted value repository 126. As another example, if one or more new values 124 are added to the extracted value repository 126 or an existing value 124 is modified, at least a subset of the queries 140 in the query repository 142 may be applied to the new or modified value(s) 124. The determined query results 144 responsive to a new or modified query 140 or value 124 may be added to the query result repository 146 or may replace existing query results 144.

A query editing module 148 may also be in communication with the query repository 142. The query editing module 148 may be used to create or modify queries 140 based on user input from one or more user devices 114. For example, the query editing module 148 may receive query input 150 from a user device 114 including indications of filters, terms, threshold values, and so forth, which may be used to generate one or more queries 140.

A result presenting module 152 in communication with the query result repository 146 may present one or more subsets of information from the query result repository 146 as a report 154 or another type of output (e.g., a graph, a table, a list, etc.). Results 154 in the query result repository 146 may be used as inputs to populate fields, cells, or other data structure elements in one or more report layouts 156 stored in a result layout repository 158. In some implementations, the result presenting module 152 may determine particular fields or indicators of values 124 present in a report layout 156. At least a subset of the results 144 in the query result repository 146 may be used to populate the report layout 156. For example, the result presenting module 152 may access a report layout 156 relating to cardiology studies, having fields relating to the ejection fraction for one or more studied hearts. The result presenting module 152 may determine a subset of the results 144 that include a value 124 associated with a heart ejection fraction. One or more of the corresponding results 144 may be used to populate the report layout 156 to generate a report 154 for transmission to a user device 114.

A layout editing module 160 associated with the result layout repository 158 may be used to create, remove, or modify report layouts 156. For example, layout input 162 from a user device 114 may indicate fields, types of values 124, particular values 124, types of DSRs 104, and so forth, as well as formatting and visual elements. The layout editing module 160 may use the layout input 162 to generate or modify one or more report layouts 156.

Figure 2:
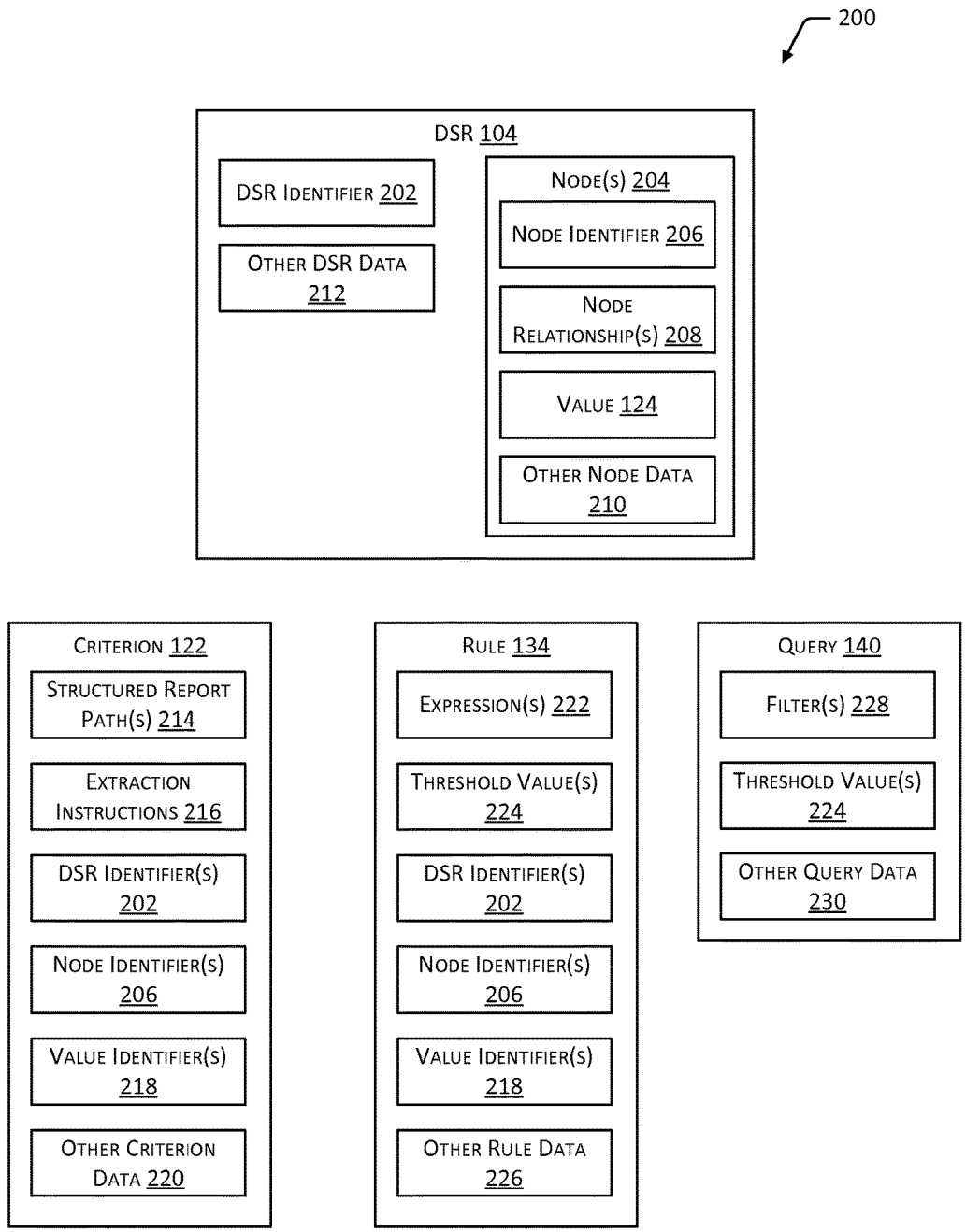
FIG. 2 depicts block diagrams illustrating an example DSR, criterion, rule, and query.

FIG. 2 depicts block diagrams 200 illustrating an example DSR 104, criterion 122, rule 134, and query 140. A DSR 104 may include a DSR identifier 202, such as a name, title, or other data indicative of a particular DSR 104 that may be used to differentiate the DSR 104 from other DSRs 104 or other types of data. The DSR identifier 202 may include one or more of alphanumeric data, image data, or audio data. For example, a DSR 104 associated with an adult echocardiography study may have a DSR identifier 202 of "Adult Echocardiography Procedure Report", while a DSR 104 associated with a vascular ultrasound study may have a DSR identifier 202 of "Vascular Ultrasound Procedure Report". As described previously, a DSR 104 may include one or more nodes 204, and at least a subset of the nodes 204 may contain values 124. In some implementations, the DSR identifier 202 associated with a DSR 104 may be a value 124 associated with a node 204. For example, the root or parent node 204 of a DSR 104 associated with an adult echocardiography study may have the value 124 "DCM/125200/Adult Echocardiography Procedure_Report". The root or parent node 204 of a DSR 104 associated with a vascular ultrasound study may have the value 124 "DCM/125100/Vascular Ultrasound Procedure_Report". In other implementations, the DSR identifier 202 may be separate from the one or more nodes 204.

The nodes 204 of the DSR 104 may be arranged in a tree or graph structure in which certain nodes 204 are associated with or depend from certain other nodes 204, and the associated nodes 204 are connected by edges. A node 204 may include a node identifier 206, which may include any manner of alphanumeric data, image data, audio data, and so forth, that may be used to differentiate a particular node 204 from other nodes 204. In some implementations, the node identifier 206 may indicate the type of value 124 contained in the node 204. The node identifier 206 may also indicate a type or category associated with the node 204. For example, a node identifier 206 may indicate that a particular node 204 is a container node 204, a numeric node 204, and so forth. A node 204 may also include one or more node relationships 208, which may indicate other nodes 204 associated therewith and the nature of the relationship between the nodes 204. For example, types of node relationships 208 between nodes 204 may include "contains", "has observation context", "has acquisition context", "has concept modifier", "has properties", "inferred from", or "selected from". Continuing the example, a child or target node 204 may be associated with a parent or source node 204 based on the "inferred from" node relationship 208. Specifically, the value 124 of the parent node 204 may include a conclusion, deduction, or inference made based on values 124 of one or more child nodes 204 and other nodes 204 that depend from the child node(s) 204.

Each node 204 may also include a value 124. Values 124 may include codes, such as text or alphanumeric data. For example, a value 124 may include a Boolean result (e.g., "True", "False", "Yes", "No", "Present", "Absent") indicating whether a patient is affected by a particular medical condition. A value 124 may include a name. A value 124 may include alphanumeric data representative of medical findings or impressions. Values 124 may also include numeric values 124. For example, a value 124 may include a dimension of an artery, a flow rate, and so forth. In some implementations, a value 124 may include an image, a reference to an image or a portion of an image, and so forth.

Other node data 210 may include data indicative of characteristics of the node 204, such as a type or category associated with the node 204. Other node data 210 may also include data indicative of characteristics of the value 124, such as a particular type or category associated with the value 124, a particular type of data associated with the value 124 (e.g., a numeric quantity, an alphanumeric string, etc.), units of measurement associated with the value 124, and so forth. Other node data 210 may include data indicative of characteristics of node relationships 208, such as values or characteristics associated with edges connecting the nodes 204.

In addition to the nodes 204 and DSR identifiers 202, a DSR 104 may also include other DSR data 212, such as metadata indicative of the author of a DSR 104, the time at which a DSR 104 was generated, modified, completed, or verified, a type or category associated with the DSR 104, and so forth. Other DSR data 212 may also include attributes that identify the DSR 104 as a DICOM file, such as a "SOPCIassUID", which may identify the file type of the DSR 104 as a report rather than a different type of DICOM file (e.g., an image 106). Other DSR data 212 may also include data indicative of a version associated with a DSR 104. For example, a single study may include multiple DSRs 104. Continuing the example, the latest, final DSR 104 for a study may include the most recent impressions and measurements, as signed by a physician. An earlier DSR 104 for the study may include a first preliminary report signed by a technician, prior to participation by the physician, which may be used in conjunction with the latest DSR 104 to calculate the total time required to complete the study. An earlier DSR 104 may also include machine-generated reports indicative of measurement values before a preliminary or final DSR 104 was created. The other DSR data 212 may indicate the relationship between related DSRs 104, enabling a group of related reports to be determined and accessed.

A criterion 122 may be used to locate particular nodes 204 within one or more DSRs 104 and to extract values 124 from one or more of the nodes 204. The criterion 122 may include one or more structured report paths 214. Structured report paths 214 may include an indication of the location of one or more particular nodes 204 within a DSR 104. Structured report paths 214 may indicate node types, names, identifiers, and so forth. For example, a structured report path 214 may be configured to determine a value 124 associated with an ejection fraction in a DSR 104. The structured report path 214 may include logic configured to determine a container-type node 204 having a node identifier 206 of "DCM/121070/Findings". While multiple DSRs 104 may include a container-type node 204 having this node identifier 206, the logic of the structured report path 214 may further specify that values 124 should be extracted only from a subset of the container-type nodes 204 that are associated with a dependent concept modifier-type node 204 with the node identifier 206 of "SRT/G-C171/Laterality" and a value 124 of "SRT/G-A100/Right". The logic of the structured report path 214 may further specify that this subset of container-type nodes 204 may contain a numeric-type node 204 having the node identifier 206 of "DCM/122211/Left Ventricular Ejection Fraction". As another example, a structured report path 214 may be configured to locate multiple nodes 204, such as all child nodes 204 associated with a container-type node 204 having the node identifier 206 of "DCM/121109/Indications for Procedure". As yet another example, a structured report path 214 may be configured to aggregate or manipulate values 124. Continuing the example, a structured report path 214 may be configured to locate multiple numeric nodes 204 having the node identifier 206 of "LN/11726-7/Peak Velocity" and normalize each value 124 in these nodes 204 to a selected unit of measurement (e.g., cm/s). The criterion 122 may be configured to individually store each of the values 124, to aggregate, average, or otherwise manipulate the values 124 to determine a subsequent value 124, to store a single particular value 124 such as the maximum numerical value 124 located through this process, and so forth. In some implementations, a structured report path 214 may be used to identify whether a particular DSR 104 is suitable for processing using a criterion 122. For example, DSRs 104 that lack any node 204 having such a node identifier 206 may be excluded from further processing using the criterion 122 rather than determining a null result for a value 124 that is not present in a DSR 104.

The criterion 122 may also include extraction instructions 216, which may include one or more steps that may be used to extract a value 126 from a DSR 104. For example, in a numeric node 204, a numeric value 124 may simply be determined and provided to the extracted value repository 126. In nodes 204 containing more complex data structures, the extraction instructions 216 may indicate a manner in which a particular value 124 or a portion of a value 124 may be located within the node 204. In some implementations, such when extracting values 124 from nodes 204 that contain image data or alphanumeric codes, the extraction instructions 216 may be configured to execute one or more plug-ins, such as programs configured to perform optical character recognition (OCR) or other types of processing.

In some implementations, a criterion 122 may include one or more DSR identifiers 202. For example, a criterion 122 may be configured to process particular DSRs 104, particular types of DSRs 104, DSRs 104 having particular characteristics, and so forth. In other implementations, a criterion 122 may include one or more node identifiers 206. For example, a criterion 122 may be configured to process DSRs 104 that contain particular nodes 204, nodes 204 of a particular type or category, nodes 204 having particular characteristics, and so forth. In other implementations, a criterion 122 may include one or more value identifiers 218. For example, a criterion 122 may be configured to process DSRs 104 or nodes 206 having particular values 124, particular ranges of values 124, particular types or categories of values 124, values 124 having particular characteristics, and so forth.

A criterion 122 may be used to process one or more DSRs 104 by determining correspondence between DSRs 104 stored in association with the PACS server 102 and one or more of the DSR identifiers 202, node identifiers 206, or value identifiers 218 associated with the criterion 122. In other implementations, the criterion 122 may be used to process one or more DSRs 104 by determining correspondence between the structured report path(s) 214 of the criterion 122 and one or more of the DSRs 104 stored in association with the PACS server 102. For example, the criterion 122 may be used to identify a subset of DSRs 104 having at least one node 204 that corresponds to the structured report path(s) 214. For each corresponding DSR 104, the criteria processing module 118 may determine the value 124 at the node 204 corresponding to the structured report path 214 and store the value 124, such as in a hash map or database. In some implementations, a criterion 122 may also include a rule 134 or script that may be executed to manipulate or modify one or more values 124 or to determine additional values 124 based on the values 124 determined from the DSRs 104. For example, the extraction instructions 216 may cause extraction of one or more values 124 and storage in a temporary data structure, such as a hash map. The extracted values 124 may then be used to determine a subsequent value 124 by applying one or more rules 134 to the extracted values 124. The hash map may then be deleted. As another example, the extraction instructions 216 may cause extraction of one or more values 124 and storage in a persistent format, such as a table or database. In some implementations, persistently stored values 124 may also be used to determine subsequent values 124, such as by application of one or more rules 134.

Other criterion data 220 may include metadata indicative of the author of a criterion 122, the times at which a criterion 122 was generated or modified, the times at which a criterion 122 was previously applied to a DSR 104, an identifier associated with the criterion 122, and so forth. Other criterion data 220 may also include configurations associated with a plug-in or other method used to extract values 124 from nodes 204, such as references to libraries. Other criterion data 220 may further include other characteristics of DSRs 104 that may be used to filter the DSRs 104 to which the criterion 122 is applied. For example, a criterion 122 may be configured for use with DSRs 104 based on the title of a DSR 104, a verification or completeness status of the DSR 104, and so forth.

Rules 134 may be used to process or manipulate extracted values 124, to determine additional values 124 based on the extracted values 124, and so forth. In some implementations, a rule 134 may be included within a criterion 122. In other implementations, one or more rules 134 may be separate and distinct from the criteria 122. As described previously, a rule 134 may be used to modify an extracted value 124. In other implementations, a rule 134 may be used to determine one or more additional values 124 based on one or more of the extracted values 124. For example, a rule 134 may be configured to determine whether multiple extracted values 124 fall within or outside of particular ranges, the relationships between particular extracted values 124, and the combinations of such relationships. Based on this determination, the rule 134 may cause generation of an additional value 124. For example, an additional value 124 may include an alphanumeric code indicating that the extracted values 124 indicate a particular medical condition, even in cases where findings or impressions regarding the particular medical condition may not have been present in one or more of the DSRs 104. Subsequent queries 140 applied to the extracted value repository 126 may determine DSRs 104 indicative of the particular medical condition by filtering for the additional value 124 determined by the rule 134. As another example, a rule 134 may determine whether values 124 indicative of a particular dimension, flow rate, or other value exceed or fall below a threshold number. The rule 134 may cause generation of additional values 124, such as Boolean codes indicating whether a particular extracted value 124 exceeds or falls below a threshold number. Subsequent queries 140 applied to the extracted value repository 126 may determine DSRs 104 that exhibit a particular measurement by filtering for the additional value 124 determined by the rule 134.

A rule 134 may include one or more expressions 222. In some implementations, the rule 134 may also include one or more threshold values 224. Expressions 222 may include algorithms, equations, operators, and so forth, that may be used to modify a value 124, compare the value 124 to other values 124, compare the value 124 to threshold values 224, and so forth. For example, expressions 222 may include conditional language (e.g., "If", "Then", "Else"), mathematical operators (e.g., =, !=, <, >, <=, >=, +, −, *, /), numerals, alphanumeric strings, and so forth. For example, where "V" is a theoretical value 124 extracted from a DSR 104, a rule 134 may read:

If (V !=null) {String status="<3 cm"; If (aaa>=3) {status=">=3 cm";}
results["category"]=status;}

Application of the above rule 134 to one or more DSRs 104 would cause generation of a new value 124 for each DSR 104 in which the value 124 "V" was not a null value 124. For DSRs 104 having a particular value 124 greater than or equal to a threshold value 224 of 3, a new value 124 would be generated having the alphanumeric string ">=3 cm". For DSRs for which this particular value 124 did not equal or exceed the threshold value 224 of 3, the new value 124 would be provided with the alphanumeric string "<3 cm".

In some implementations, a rule 134 may include one or more DSR identifiers 202, node identifiers 206, or value identifiers 218. For example, correspondence between a value 124, DSR 104, or node 204 from which the value 124 was extracted and a rule 134 may be used to determine whether the rule 134 is applicable to the extracted value 124. In other implementations, a rule 134 may be a part of a criterion 122, and the rule 134 may be applied to values 124 extracted using the criterion 122. In yet other implementations, a criterion 122 may not include a rule 134, and an extracted value 124 may be stored in the extracted value repository 126 without modifying the value 124 or determining additional values 124 based on the extracted value 124.

In some implementations, a rule 134 may be generated via user input, such as the criteria input 130 used to generate one or more criteria 122. For example, a user device 114 may be provided with a GUI. Fields or selectable elements in the GUI may be mapped to or correspond to particular expressions 222. For example, user input selecting an element corresponding to heart disease may cause generation of a rule 134 with expressions 222 indicating various relationships between values 124 and threshold values 224 that may be indicative of heart disease.

Other rule data 226 may include metadata indicative of the author of a rule 134, the times at which a rule 134 was generated or modified, the times at which a rule 134 was previously applied to a value 124, an identifier associated with the rule 134, and so forth.

Queries 140 may be used to determine results 144 based on extracted values 124 and generate reports 154. In some implementations, queries 140 may be generated via user input (e.g., query input 150). The user input may include a manual query 140 provided by a human user or an automated query 140 generated by a service, computing device, and so forth. Once provided, a query 140 may be manually executed via user input or automatically executed (e.g., on a periodic or continuous basis).

A query 140 may include one or more filters 228. Filters 228 may include data indicative of particular fields or characteristics of DSRs 104, nodes 204, values 124, criteria 122, rules 134, and so forth. For example, a filter 228 may include an alphanumeric search term that corresponds to the title of a subset of DSRs 104, a numeric search term that corresponds to a range of times associated with one or more DSRs 104, an alphanumeric search term that corresponds to a particular value 124 indicative of the presence of a medical condition, and so forth. Continuing the example, a filter 228 may include search terms indicative of a particular category or value identifier 218 of a value 124 (e.g., "heart disease") and a search term indicative of a specific value 124 for that category (e.g., "True" or "Present"). Application of the query 140 to the values 124 may yield all values 124 having the value identifier 218 "heart disease" and a value 124 of "True" or "Present". Queries 140 may also include one or more threshold values 224. For example, a query 140 may include a filter 228 configured to determine all DSRs 104 associated with a PACS server 102 that indicate an aneurysm having any dimension greater than a threshold value 224 of 3 cm.

Other query data 230 may include metadata indicative of the author of a query 140, the times at which a query 140 was generated or modified, the times at which a query 140 was previously applied to one or more values 124, an identifier associated with the query 140, and so forth. Other query data 230 may also include configurations associated with the query 140 such as a frequency at which the query 140 is executed, whether the query 140 is configured to automatically execute upon receipt or modification of one or more values 124, and so forth.

Figure 3:
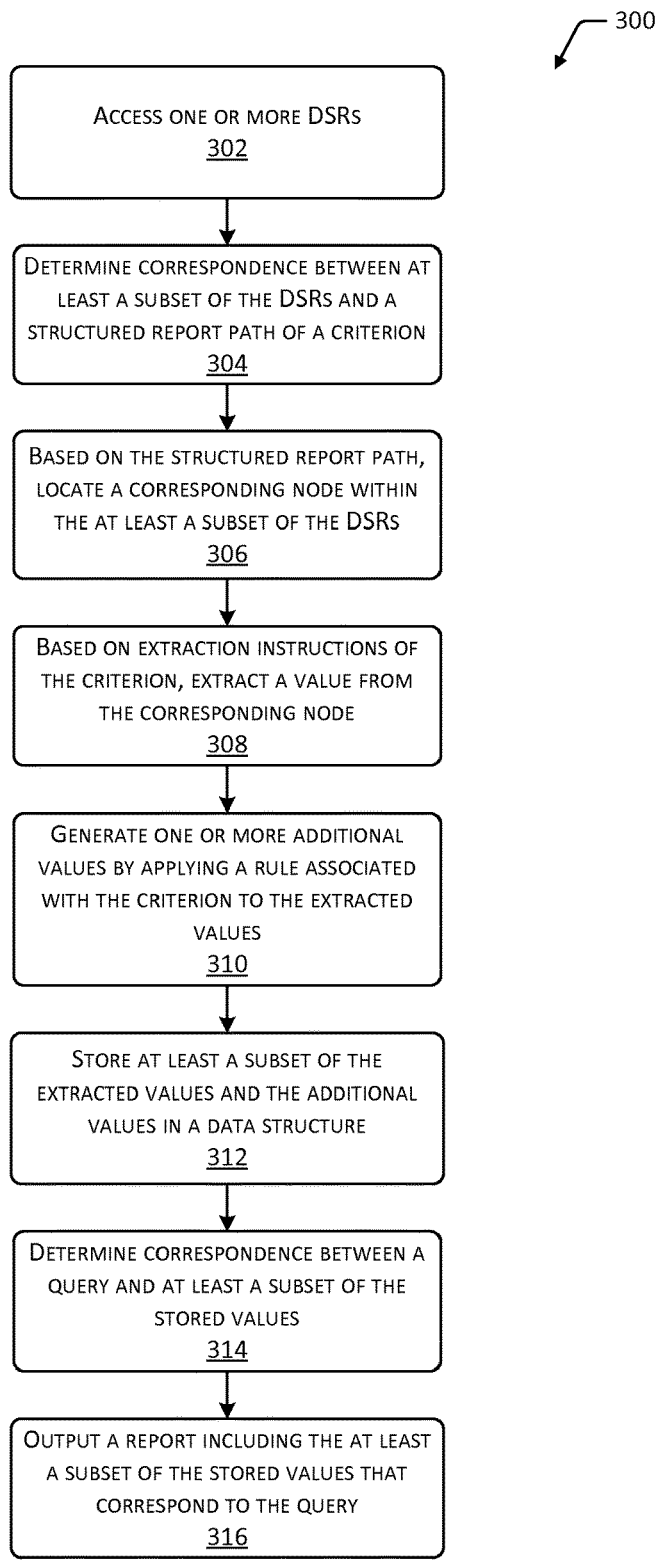
FIG. 3 is a flow diagram illustrating a method for extracting values from DSRs, generating additional values based on the extracted values, and generating a report based on one or more queries.

FIG. 3 is a flow diagram 300 illustrating a method for extracting values 124 from DSRs 104, generating additional values 124 based on the extracted values 124, and generating a report 154 based on one or more queries 140. Block 302 accesses one or more DSRs 104. Accessing DSRs 104 may include accessing all or a subset of DSRs 104 stored in association with a PACS server 102. In other implementations, accessing of DSRs 104 may include receiving one or more DSRs 104 from a user device 114 or receiving an indication of one or more particular stored DSRs 104 from the user device 114.

Block 304 determines correspondence between at least a subset of the DSRs 104 and a structured report path 214 of a criterion 122. As described previously with regard to FIG. 2, a structured report path 214 may include an indication of one or more nodes 204 within a DSR 104. Correspondence between the DSR 104 and the structured report path 214 may indicate that the DSR 104 includes one or more nodes 204 indicated by the structured report path 214. A lack of correspondence between the DSR 104 and the structured report path 214 may indicate that the DSR 104 does not include the node(s) 204 indicated by the structured report path 214 and that subsequent application of the criterion 122 to the DSR 104 may yield a null result or an error. In other implementations, determining correspondence between the DSR 104 and the structured report path 214 may include determining whether the nodes 204 of the DSR 104 indicated by the structured report path 214 include values 124. As such, the determination of correspondence between the DSR 104 and the structured report path 214 may determine a subset of DSRs 104 for which application of the criterion 122 may successfully extract a non-null value 124.

Block 306 locates a corresponding node 204 within the at least a subset of the DSRs 104 based on the structured report path 214 of the criterion 122. The structured report path 214 may include code or logic indicative of the location of a particular node 204 in a DSR 104. For example, a structured report path 214 may include a machine-readable path indicative of a particular location within the tree structure of a DSR 104, coordinates within an image or report, and so forth. One possible process for traversing a DSR 104 using a structured report path 214 is described in U.S. patent application Ser. Nos. 13/507,195; 12/932,973; and Ser. No. 11/592,608.

Block 308 extracts a value 124 from a corresponding node 204 of a DSR 104 based on extraction instructions 216 of the criterion 122. The extraction instructions 216 may include one or more steps that may be used to extract a value 124 from the DSR 104. Extraction of a value 124 may include a single step, such as copying a numeric value 124 from a numeric node 204 to the extracted value repository 126. In nodes 204 containing more complex data structures, the extraction instructions 216 may indicate a manner in which a particular value 124 or a portion of a value 124 may be located within the node 204. In some implementations, such as when extracting values 124 from nodes 204 that contain image data or alphanumeric codes, the extraction instructions 216 may be configured to execute one or more plug-ins or other programs configured to determine a particular value 124 from within image or alphanumeric data.

In some implementations, the criterion 122 may indicate that particular values 124 are to be stored, such as in a table, database, or other persistent data structure within the extracted value repository 126. In other implementations, the criterion 122 may indicate that other values 124 are to be stored temporarily, such as in a hash map or other temporary data structure, so that the values 124 may be used to determine one or more additional values 124. Some values 124 may be stored in a persistent data structure, and also used to determine additional values 124.

Block 310 generates one or more additional values 124 by applying a rule 134 associated with the criterion 122 to one or more extracted values 124. As described previously with regard to FIG. 2, a rule 134 may include one or more expressions 222 that associate extracted values 124 with one or more other extracted values 124 or threshold values 224. For example, expressions 222 may include conditional language (e.g., "If", "Then", "Else"), mathematical operators (e.g., =, !=, <, >, <=, >=, +, −, *, /), numerals, alphanumeric strings, threshold values 224, and so forth. Application of one or more rules 134 to one or more extracted values 124 may yield one or more additional values 124, which may be stored in the extracted value repository 126. For example, based on one or more extracted values 124 indicative of dimensions of a particular anatomical feature, a rule 134 may cause an additional value 124 indicative of a range of sizes or a particular medical condition to be generated and stored. In some implementations, the additional values 124 determined using one or more rules 134 may in turn be used to determine further additional values 124 via one or more of the rules 134.

Block 312 stores at least a subset of the extracted values 124 and the additional values 124 in a data structure (e.g., within the extracted value repository 126). In some implementations, the criterion 122 may include an indication regarding whether a particular value 124 is to be stored in persistent data structure in the extracted value repository 126 or in a temporary data structure that may be deleted after computing one or more additional values 124 based on the particular value 124. For example, a criterion 122 may be configured to determine DSRs 104 that indicate a mass having a diameter of 3 cm or greater. The criterion 122 may locate nodes 204 in at least a subset of the DSRs 104 that include a value 124 for one or more dimensions of a mass and store these values 124 in a hash map or another type of temporary data structure. A rule 134 associated with the criterion 122 may then be used to generate an additional value 124, such as the alphanumeric string ">=3 cm" for values 124 that indicate a mass having a diameter greater than or equal to 3 cm, and "<3 cm" for values 124 that indicate a mass with a diameter less than 3 cm. In some implementations, the additional value 124 may be stored in a persistent data structure, such as a database, and the hash map may then be deleted. Subsequent queries 140 may be used to search the extracted value repository 126 for values 124 that indicate a mass greater than or less than 3 cm by including the search string ">=3 cm" or "<3 cm", respectively, as a filter 228.

Block 314 determines correspondence between a query 140 and at least a subset of the stored values 124. For example, a query 140 may include one or more search terms or other types of filters 228 indicative of particular values 124, ranges of values 124, particular DSRs 104, identifiers associated with DSRs 104, nodes 204, or values 124, and so forth.

Block 316 may output a report 154 that includes at least a subset of the stored values 124 that correspond to the query 140. As described previously with regard to FIG. 1, one or more report layouts 156 may be selected automatically or via user input and populated with results 144 obtained by application of one or more queries 140 to values 124 in the extracted value repository 126. Reports 154 may be output to a user device 114 or stored for subsequent access. In some implementations, multiple reports 154 may be stored, aggregated, queried, and so forth.

Figure 4:
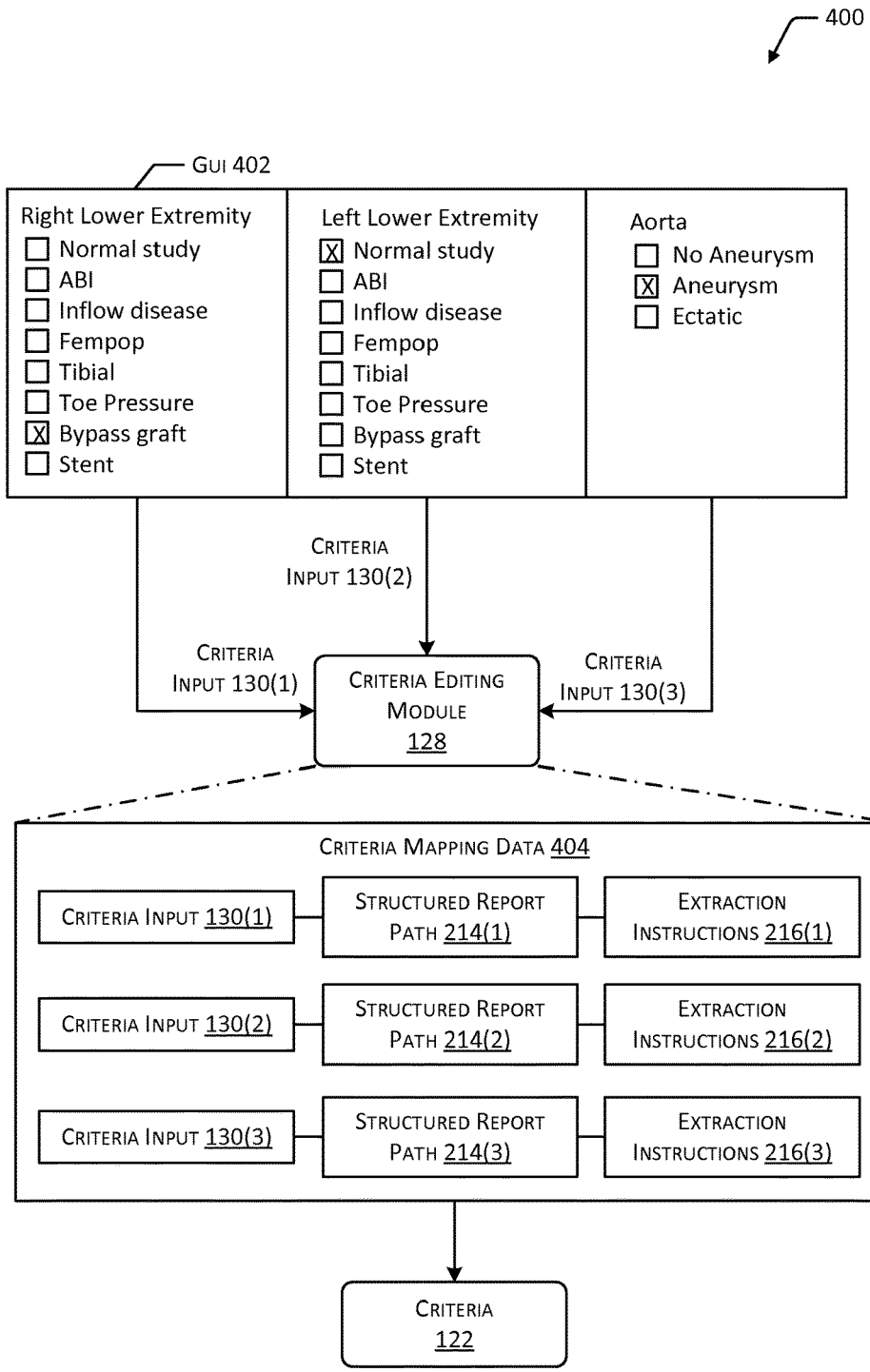
FIG. 4 is a block diagram that depicts an example graphical user interface (GUI) that may be used to generate criteria for extracting values from DSRs.

FIG. 4 is a block diagram 400 that depicts an example graphical user interface (GUI) 402 that may be used to generate criteria 122 for extracting values 124 from DSRs 104. The GUI 402 may include one or more indications of particular medical findings, impressions, or conditions that may be entered or selected via user input. In some implementations, the fields present in a GUI 402 may correspond to one or more fields produced using a report layout 156. For example, items in the GUI 402 that may be selected may correspond to fields, findings, impressions, or indications present in a report 154. Continuing the example, a user may select one or more items from a previously-generated report 154 to generate criteria 122, which may in turn be used to determine DSRs 104 having characteristics similar to those selected from the report 154.

The GUI 402 of FIG. 4 includes multiple selectable indications relating to a patient's "Right Lower Extremity", "Left Lower Extremity", and "Aorta" that may be found in a DSR 104 or in a report 154 generated based on one or more DSRs 104. First criteria input 130(1) (e.g., user input) may be received from a user device 114 to which the GUI 402 is provided, the first criteria input 130(1) indicating a first finding or impression (e.g., "Bypass graft" associated with the "Right Lower Extremity"). Second criteria input 130(2) may be associated with a second finding or impression (e.g., "Normal study" associated with the "Left Lower Extremity"). Third criteria input 130(3) may be associated with a third finding or impression (e.g., "Aneurysm" associated with "Aorta").

The criteria editing module 128 may receive the criteria input 130 and determine correspondence between the criteria input 130 and criteria mapping data 404. The criteria mapping data 404 may associate particular criteria input 130 with a structured report path 214 and extraction instructions 216 configured to locate values 124 within DSRs 104 that correspond to the criteria input 130 and extract the values 124 from the DSRs 104. For example, the first criteria input 130(1) may correspond to a first structured report path 214(1) that indicates the location of a node 204 containing values 124 associated with a bypass graft within a patient's right lower extremity. The first criteria input 130(1) may also correspond to a first set of extraction instructions 216(1) configured to extract values 124 from such a node 204. The second criteria input 130(2) may similarly correspond to a second structured report path 214(2) and a second set of extraction instructions 216(2). The third criteria input 130(3) may correspond to a third structured report path 214(3) and a third set of extraction instructions 216(3). Based on the corresponding structured report paths 214 and extraction instructions 216, the criteria editing module 128 may generate one or more criteria 122.

Figure 5:
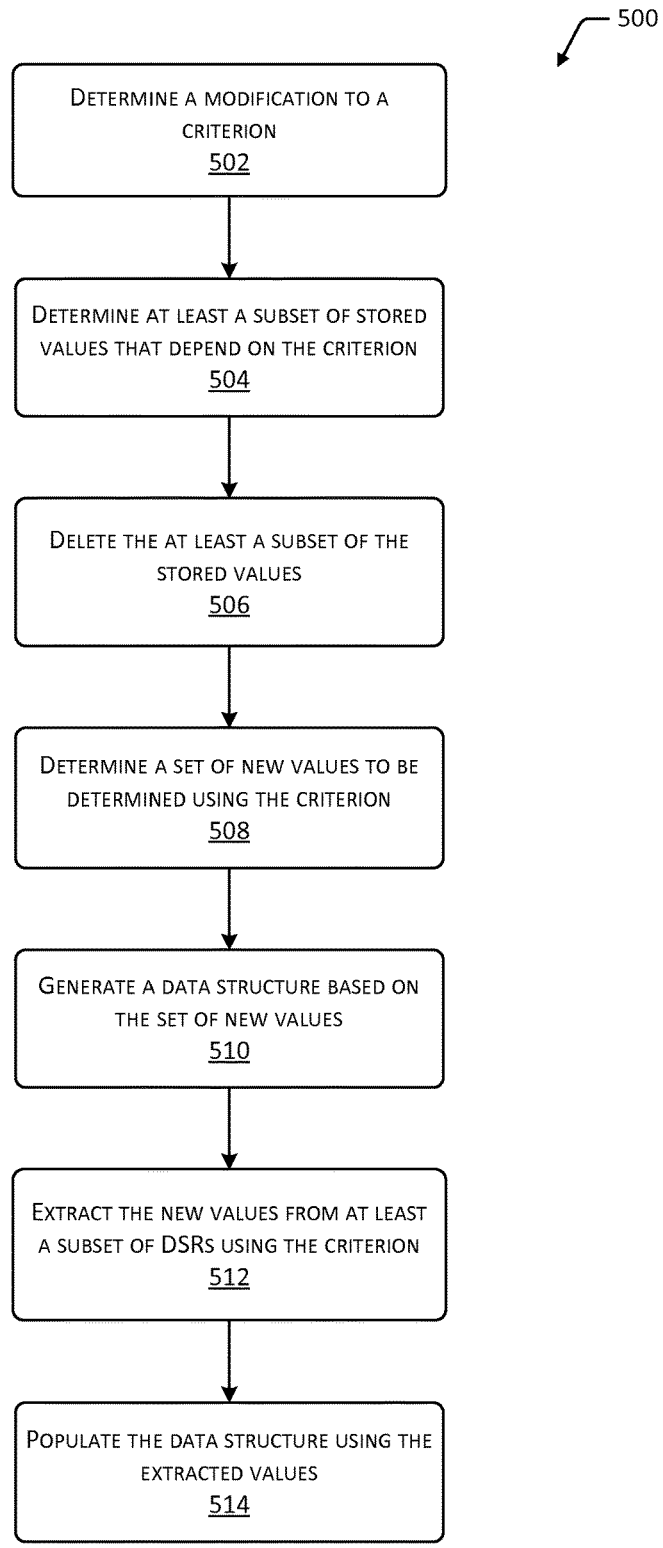
FIG. 5 is a flow diagram illustrating a method for determining values subsequent to a modification of a criterion.

FIG. 5 is a flow diagram 500 illustrating a method for determining values 124 subsequent to a modification of a criterion 122. Block 502 determines a modification to a criterion 122. Criteria input 130 from a user device 114 or another source may be used to change one or more parts of a criterion 122. For example, a user may add, remove, or modify one or more rules 134 or scripts associated with a criterion 122, add or remove values 124 that are extracted by the criterion 122, or modify, add, or remove structured report paths 214.

Block 504 determines at least a subset of stored values 124 that depend on the criterion 122. In some implementations, one or more values 124 or the location within a data structure where the value(s) 124 are stored may include a flag, identifier, or other metadata indicating the criterion 122 that was used to generate and store the value(s) 124. For example, correspondence between the flag, identifier, or other metadata and an identifier associated with the criterion 122 may be used to determine the values 124 associated with the criterion 122. In other implementations, metadata associated with the criterion 122 may indicate the values 124 determined therefrom or a location of the values 124 in a data structure. In still other implementations, the criteria processing module 118 may at least partially execute the unmodified criterion 122 to determine the values 124 that depend therefrom.

Block 506 deletes at least a subset of the stored values 124. In some implementations, a modified criterion 122 may be used to overwrite existing values 124, and block 506 may not be performed. However, in other implementations, deletion of the values 124 that depend from the criterion 122 may ensure that no extraneous values 124 remain in the extracted value repository 126. For example, a criterion 122 may initially extract three values 124 from a set of DSRs 104. The modified version of the criterion 122 may only extract two values 124. If the modified version of the criterion 122 is used to overwrite the previous values 124 in the extracted value repository 126, the third value 124, which depends from the unmodified version of the criterion 122, would remain stored. Deletion of each of the values 124 that depend from criterion 122 may prevent the retention of an extraneous value 124. For example, if the three values 124 initially determined using a criterion 122 are deleted before the modified version of the criterion 122 is used to extract two values 124, the extraneous third value 124 will not be retained.

Block 508 determines a set of new values 124 to be determined using the criterion 122. For example, the criteria processing module 118 may determine value identifiers 218 or other data indicative of the types of values 124 to be extracted using the criterion 122 and a location or data structure in which the values 124 may be stored. In some implementations, the criteria processing module 118 may at least partially execute the modified criterion 122 to determine the set of new values 124.

Block 510 generates a data structure based on the set of new values 124. For example, the criteria processing module 118 may add rows or columns to a table that correspond to one or more values 124, labels or headers to portions of a data structure that correspond to value identifiers 218, and so forth. Data structures for storing the values 124 may include any manner of database, table, list, tree structure, or other types of data structures.

Block 512 extracts the new values 124 from at least a subset of DSRs 104 using the criterion 122. As described previously with regard to FIG. 3, the modified criterion 122 may include structured report paths 214 that may be used to locate nodes 204 within DSRs 104 that contain particular values 124. The criterion 122 may also include extraction instructions 216 that may be used to extract values 124 from the nodes 204 and store the values 124 in assigned locations in the data structure. In some implementations, the modified criterion 122 may include one or more rules 134 or scripts that may be used to determine additional values 124 based on the extracted values 124.

Block 514 populates the data structure using the extracted values 124. In some implementations, the extracted values 124 may be stored in the data structure. In other implementations, additional values 124 determined based on the extracted values 124 may be stored in the data structure. In still other implementations, a combination of extracted values 124 and additional values 124 may be stored in the data structure.

The method illustrated in FIG. 5 may also be performed if a DSR 104 is modified. For example, if a modification to a DSR 104 is determined, the values 124 determined based on the application of one or more criteria 122 to that DSR 104 may be deleted. New values 124 corresponding to the modified DSR 104 may be determined and populated into a data structure.

Figure 6:
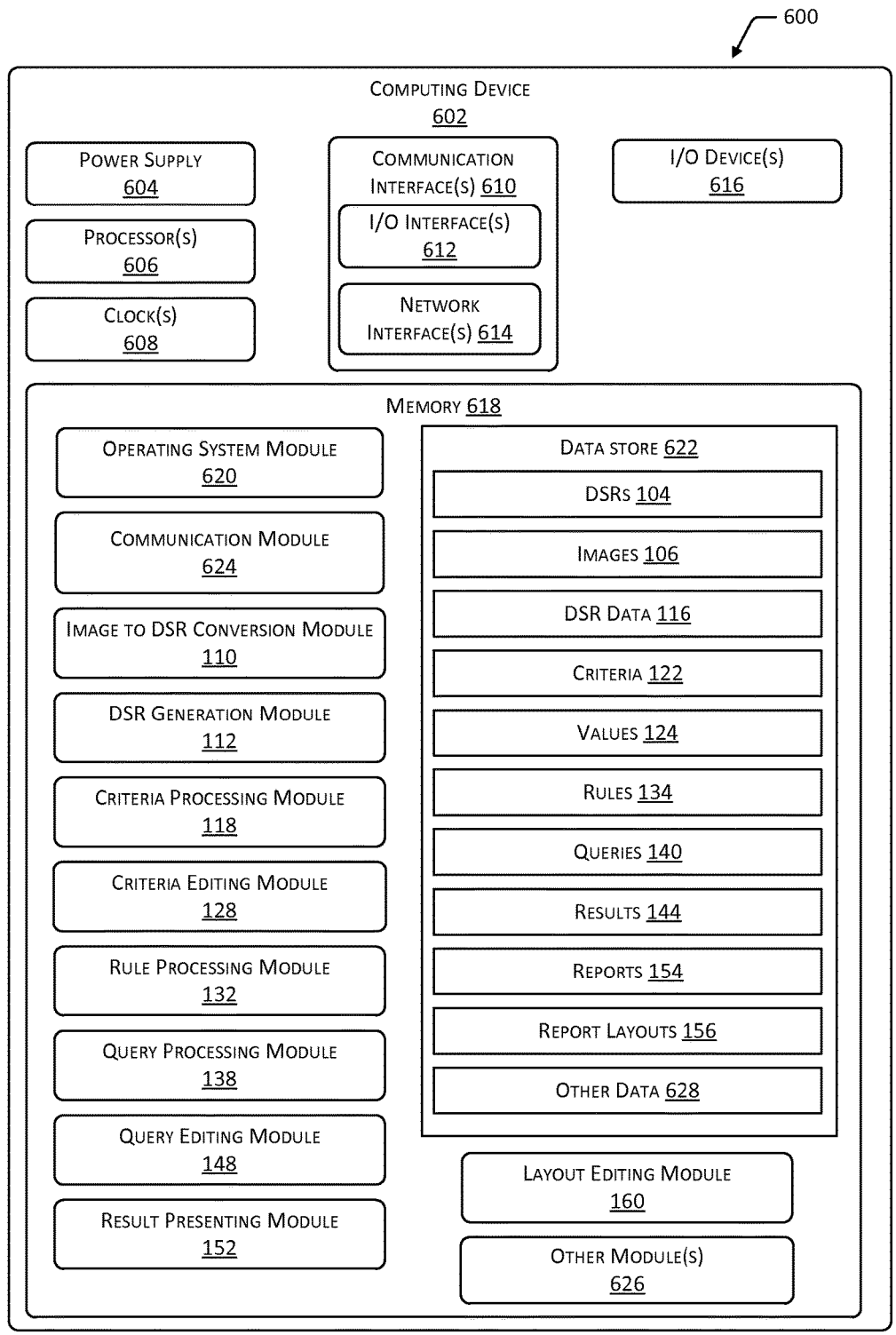
FIG. 6 is a block diagram illustrating a computing device within the scope of the present disclosure.

FIG. 6 is a block diagram 600 illustrating a computing device 602 within the scope of the present disclosure. The computing device 602 may include one or more PACS servers 102, user devices 114, or other computing devices 602 in communication therewith.

One or more power supplies 604 may be configured to provide electrical power suitable for operating the components of the computing device 602. In some implementations, the power supply 604 may include a rechargeable battery, fuel cell, photovoltaic cell, power conditioning circuitry, and so forth.

The computing device 602 may include one or more hardware processor(s) 606 (processors) configured to execute one or more stored instructions. The processor(s) 606 may include one or more cores. One or more clocks 608 may provide information indicative of date, time, ticks, and so forth. For example, the processor(s) 606 may use data from the clock 608 to generate a timestamps when DSRs 104, criteria 122, rules 134, and queries 140 are created, modified, or executed. Data from the clock 608 may also be used to trigger a preprogrammed action. For example, a query 140 may be preprogrammed for execution at one or more predetermined times or on a periodic basis.

The computing device 602 may include one or more communication interfaces 610, such as input/output (I/O) interfaces 612, network interfaces 614, and so forth. The communication interfaces 610 may enable the computing device 602, or components of the computing device 602, to communicate with other computing devices 602 or components of other computing devices 602. The I/O interfaces 612 may include interfaces such as Inter-Integrated Circuit (I2C), Serial Peripheral Interface bus (SPI), Universal Serial Bus (USB) as promulgated by the USB Implementers Forum, RS-232, and so forth.

The I/O interface(s) 612 may couple to one or more I/O devices 616. The I/O devices 616 may include any manner of input device or output device associated with the computing device 602. For example, I/O devices 616 may include touch sensors, keyboards, mouse devices, microphones, image sensors (e.g., cameras), scanners, displays, speakers, haptic devices, printers, and so forth. In some implementations, the I/O devices 616 may be physically incorporated with the computing device 602 or may be externally placed.

The network interfaces 614 may be configured to provide communications between the computing device 602 and other devices, such as the I/O devices 616, routers, access points, and so forth. The network interfaces 614 may include devices configured to couple to one or more networks including local area networks (LANs), wireless LANs, wide area networks (WANs), wireless WANs, and so forth. For example, the network interfaces 614 may include devices compatible with Ethernet, Wi-Fi®, Bluetooth®, ZigBee®, Z-Wave, 3G, 4G, LTE, and so forth.

The computing device 602 may include one or more busses or other internal communications hardware or software that allows for the transfer of data between the various modules and components of the computing device 602.

As shown in FIG. 6, the computing device 602 may include one or more memories 618. The memory 618 may include one or more CRSM. The CRSM may be any one or more of an electronic storage medium, a magnetic storage medium, an optical storage medium, a quantum storage medium, a mechanical computer storage medium, and so forth. The memory 618 may provide storage of computer-readable instructions, data structures, program modules, and other data for the operation of the computing device 602. A few example modules are shown stored in the memory 618, although the same functionality may alternatively be implemented in hardware, firmware, or as a system on a chip (SoC).

The memory 618 may include one or more operating system (OS) modules 620. The OS module 620 may be configured to manage hardware resource devices such as the I/O interfaces 612, the network interfaces 614, the I/O devices 616, and to provide various services to applications or modules executing on the processors 606. The OS module 620 may implement a variant of the FreeBSD™ operating system as promulgated by the FreeBSD Project; UNIX™ or a UNIX-like operating system; a variation of the Linux™ operating system as promulgated by Linus Torvalds; the Windows® operating system from Microsoft Corporation of Redmond, Wash., USA; or other operating systems.

A data store 622 and one or more of the following modules may also be stored in the memory 618. The modules may be executed as foreground applications, background tasks, daemons, and so forth. The data store 622 may use a flat file, database, linked list, tree, executable code, script, or other data structure to store information. In some implementations, the data store 622 or a portion of the data store 622 may be distributed across one or more other devices including other computing devices 602, network attached storage devices, and so forth. The data store 622 may include, for example, the criteria repository 120, the extracted value repository 126, the query repository 142, the query result repository 146, the result layout repository 158, or other repositories configured to store images 106, DSRs 104, extracted values 124, criteria 122, rules 134, queries 140, reports 154, and so forth.

A communication module 624 may be configured to establish communications with one or more other computing devices 602, such as user devices 114 and PACS servers 102. The communications may be authenticated, encrypted, and so forth.

The memory 618 may also store the image to DSR conversion module 110 and the DSR generation module 112. As described previously with regard to FIG. 1, the image to DSR conversion module 110 may generate DSRs 104, such as by populating DSR templates, by analyzing images 106 and other DICOM data, and so forth. Possible image to DSR conversion modules 110 are described in U.S. patent application Ser. Nos. 13/507,195; 12/932,973; and Ser. No. 11/592,608. The DSR generation module 112 may be used to generate DSRs 104 based on user input DSR data 116 or preexisting DSR data 116 stored in association with the computing device 602, such as images 106, text, and so forth.

The memory 618 may also store the criteria processing module 118, the criteria editing module 128, and the rule processing module 132. The criteria processing module 118 may be used to determine particular DSRs 104 to which a criteria 122 may be applied, such as by determining correspondence between the structured report path 214 of a criterion 122 and a subset of DSRs 104 stored in the data store 622. The criteria processing module 118 may also apply criteria 122 to DSRs 104 by locating nodes 204 within the DSRs 104 based on the structured report path 214 and locating and extracting values 124 within the nodes 104 based on extraction instructions 216. The criteria processing module 118 may further generate or modify a temporary or persistent data structure into which one or more of the extracted values 124 may be stored. In some implementations, the rule processing module 132 may determine one or more additional values 124 based on the extracted values 124 by applying one or more rules 134 to the extracted values 124.

The criteria editing module 128 may be used to enable new criteria 122 to be generated or existing criteria 122 to be modified, such as through use of a GUI 402 provided to a user device 114. In other implementations, user input to create or modify a criterion 122 may include alphanumeric data, such as a structured report path 214 or code that may be used as extraction instructions 216 or rules 134.

The memory 618 may also store the query processing module 138 and the query editing module 148. The query editing module 148 may be used to generate queries 140 based on user input, the queries 140 including filters 228, threshold values 224, and so forth, that may be used to determine particular DSRs 104 or values 124. The query processing module 138 may be used to apply the filters 228 and other portions of the queries 140 to stored values 124 to determine results 144 indicative of particular values 124, DSRs 104, and so forth. The memory 618 may also store the result presenting module 152, which may generate reports 154 based on the results 144 of the query 140 and one or more report layouts 156. As described with regard to FIG. 1, report layouts 156 may be generated or modified using the layout editing module 160.

Other modules 626 may also be present in the memory 618. For example, encryption modules may be used to encrypt and decrypt communications between computing devices 602. Authentication modules may be used to authenticate communications sent or received by computing devices 602. Other modules 626 may further include separate modules for processing user input, natural language processing for determining queries 140 based on alphanumeric data received from user devices 114, and so forth.

Other data 628 within the data store 622 may include user input data, such as configurations and settings associated with computing devices 602. Other data 628 may include security data, such as encryption keys and schema, access credentials, and so forth.

In different implementations, different computing devices 602 may have different capabilities or capacities. For example, PACS servers 102 may have significantly more processor 606 capability and memory 618 capacity compared to the processor 606 capability and memory 618 capacity of user devices 114.

The processes discussed in this disclosure may be implemented in hardware, software, or a combination thereof. In the context of software, the described operations represent computer-executable instructions stored on one or more computer-readable storage media that, when executed by one or more hardware processors, perform the recited operations. Generally, computer-executable instructions include routines, programs, objects, components, data structures, and the like that perform particular functions or implement particular abstract data types. Those having ordinary skill in the art will readily recognize that certain steps or operations illustrated in the figures above may be eliminated, combined, or performed in an alternate order. Any steps or operations may be performed serially or in parallel. Furthermore, the order in which the operations are described is not intended to be construed as a limitation.

Embodiments may be provided as a software program or computer program product including a non-transitory computer-readable storage medium having stored thereon instructions (in compressed or uncompressed form) that may be used to program a computer (or other electronic device) to perform processes or methods described in this disclosure. The computer-readable storage medium may be one or more of an electronic storage medium, a magnetic storage medium, an optical storage medium, a quantum storage medium, and so forth. For example, the computer-readable storage media may include, but is not limited to, hard drives, floppy diskettes, optical disks, read-only memories (ROMs), random access memories (RAMs), erasable programmable ROMs (EPROMs), electrically erasable programmable ROMs (EEPROMs), flash memory, magnetic or optical cards, solid-state memory devices, or other types of physical media suitable for storing electronic instructions. Further, embodiments may also be provided as a computer program product including a transitory machine-readable signal (in compressed or uncompressed form). Examples of transitory machine-readable signals, whether modulated using a carrier or unmodulated, include, but are not limited to, signals that a computer system or machine hosting or running a computer program can be configured to access, including signals transferred by one or more networks. For example, the transitory machine-readable signal may comprise transmission of software by the Internet.

Separate instances of these programs can be executed on or distributed across any number of separate computer systems. Although certain steps have been described as being performed by certain devices, software programs, processes, or entities, this need not be the case, and a variety of alternative implementations will be understood by those having ordinary skill in the art.

Additionally, those having ordinary skill in the art will readily recognize that the techniques described above can be utilized in a variety of devices, environments, and situations. Although the subject matter has been described in language specific to structural features or methodological acts, it is to be understood that the subject matter defined in the appended claims is not necessarily limited to the specific features or acts described. Rather, the specific features and acts are disclosed as exemplary forms of implementing the claims.

What is claimed is:

1. A system comprising:
   one or more memories storing computer-executable instructions; and
   one or more hardware processors configured to execute the computer-executable instructions to:
      access one or more DICOM structured reports including one or more nodes containing values, wherein the one or more DICOM structured reports include a first format that is not queryable using an online analytical processing tool;
      generate a graphical user interface including one or more selectable features indicative of one or more of: medical findings, medical impressions, or medical conditions of a DICOM structured report;
      receive user input via the graphical user interface, wherein the user input indicates at least a subset of the one or more selectable features;
      determine first correspondence between the one or more selectable features and criterion mapping data that associates selectable features with criteria, wherein the first correspondence indicates a particular criterion that corresponds to the one or more selectable features, and wherein the particular criterion includes a structured report path and extraction instructions, the structured report path configured to locate a particular node within the one or more DICOM structured reports, and the extraction instructions configured to extract a value from the particular node;
      determine, based on the particular criterion, the structured report path and the extraction instructions;
      determine second correspondence between the structured report path of the criterion and at least a subset of the one or more DICOM structured reports, the second correspondence indicating that the at least a subset of the one or more DICOM structured reports include the particular node corresponding to the structured report path;
      based on the structured report path, access the particular node in the at least a subset of the DICOM structured reports;
      based on the extraction instructions, determine one or more first values corresponding to the particular node for the at least a subset of the DICOM structured reports;
      store the one or more first values for the at least a subset of the DICOM structured reports in a data structure associated with a study that corresponds to the at least a subset of the one or more DICOM structured reports that include the particular node, wherein the data structure includes a second format that is queryable using the online analytical processing tool;
      determine at least one rule associated with the criterion, the at least one rule associating at least one second value with the one or more first values, wherein the at least one second value is not included in the at least a subset of the one or more DICOM structured reports;
      based on the one or more first values and the at least one rule, determine the at least one second value;
      store the at least one second value in the data structure;
      access a query including one or more filters;
      apply the one or more filters of the query to the data structure to determine a query result based on correspondence between the one or more filters, the one or more first values, and the at least one second value; and
      generate a report indicative of the query result, wherein the report includes an indication of the at least one second value not included in the at least a subset of the one or more DICOM structured reports.

2. The system of claim 1, further comprising computer-executable instructions to:
   receive, from one or more of a user device or an imaging device, one or more of:

the one or more DICOM structured reports;
user input selecting the one or more DICOM structured reports; or
one or more of user input or image data configured to cause generation of the one or more DICOM structured reports.

3. The system of claim 1, further comprising computer-executable instructions to:
delete at least one first value of the one or more first values from the data structure subsequent to determining the at least one second value and storing the at least one second value in the data structure.

4. The system of claim 1, further comprising computer-executable instructions to:
determine a modification to the criterion, forming a modified criterion;
delete the one or more first values and the at least one second value that were determined using the criterion;
based on the modified criterion, determine one or more third values; and
store the one or more third values in the data structure.

5. The system of claim 1, further comprising computer-executable instructions to:
determine a modification to a first DICOM structured report of the one or more DICOM structured reports;
determine at least a subset of the one or more first values and the at least one second value associated with the first DICOM structured report;
delete the at least a subset of the one or more first values and the at least one second value from the data structure;
based on the structured report path, access the particular node in the one of the one or more DICOM structured reports;
based on the extraction instructions, determine a third value corresponding to the particular node for the one of the one or more DICOM structured reports;
store the third value in the data structure;
based on the third value and the at least one rule, determine at least one fourth value; and
store the at least one fourth value in the data structure.

6. A method comprising:
accessing at least one DICOM structured report, wherein the at least one DICOM structured report includes a first format that is not queryable;
accessing a criterion for locating a first value in the at least one DICOM structured report wherein the criterion includes a structured report path indicating a node in the DICOM structured report and extraction instructions for extracting the first value from the node;
determining correspondence between the structured report path of the criterion and the node of at least one DICOM structured report, the correspondence indicating that the at least one DICOM structured report includes the node indicated in the structured report path;
based on the extraction instructions associated with the criterion, determine the first value contained in the node of the at least one DICOM structured report;
generate a first data structure configured to contain the first value;
store the first value in the first data structure;
based on the first value and a rule associated with the criterion, determine a second value;
store the second value in a second data structure, wherein the second data structure includes a second format that is queryable;
receive a query that includes one or more filters; and
based on second correspondence between the query and the second value in the second data structure, generate output indicative of the second value.

7. The method of claim 6, further comprising:
providing a user interface to a user device, the user interface including one or more elements indicative of one or more of: medical findings, medical impressions, or medical conditions;
receiving user input via the user interface, the user input indicating at least a subset of the one or more elements;
determining third correspondence between the at least a subset of the one or more elements and criterion mapping data that associates the at least a subset of the one or more elements with the structured report path and the extraction instructions;
based on the third correspondence, determining the structured report path and the extraction instructions that correspond to the at least a subset of the one or more elements; and
generating the criterion based on the structured report path and the extraction instructions.

8. The method of claim 6, wherein the first data structure includes a temporary data structure, the method further comprising deleting one or more of the first value or the first data structure subsequent to determining the second value.

9. The method of claim 6, wherein the first data structure includes a persistent data structure, the method further comprising generating the output further indicative of the first value.

10. The method of claim 6, wherein the second value is not included in the at least one DICOM structured report.

11. The method of claim 6, further comprising:
receiving user input indicative of a report layout, the report layout including one or more fields;
determining correspondence between the one or more fields of the report layout and the second value; and
populating at least one of the one or more fields with the second value to form a report, wherein the output includes the report.

12. The method of claim 6, further comprising:
determining a modification to one or more of the structured report path or the extraction instructions of the criterion to form a modified criterion;
based on the modified criterion, determining correspondence between the structured report path and one or more DICOM structured reports;
based on the modification and the extraction instructions determining a third value contained in the one or more DICOM structured reports;
generating a third data structure configured to contain the third value; and
storing the third value in the third data structure.

13. The method of claim 12, further comprising:
subsequent to determining the third value, replacing one or more of the first value or the second value with corresponding values associated with the modified criterion.

14. The method of claim 6, further comprising:
determining a modification to the at least one DICOM structured report, forming a modified DICOM structured report;
determining correspondence between the structured report path and the modified DICOM structured report;
based on the modified DICOM structured report and the extraction instructions determining a third value contained in the modified DICOM structured report;

generating a third data structure configured to contain the third value; and storing the third value in the third data structure.

15. The method of claim 14, further comprising:

subsequent to determining the third value, determining one or more of the first value or the second value associated with the modified DICOM structured report.

16. A system comprising:

one or more memories storing computer-executable instructions; and one or more hardware processors configured to execute the computer-executable instructions to:

provide a user interface to a user device, the user interface including one or more elements indicative of one or more of: medical findings, medical impressions, or medical conditions;

receive user input via the user interface, the user input indicating at least a subset of the one or more elements;

determine first correspondence between the at least a subset of the one or more elements and criterion mapping data associating structured report paths with the one or more elements, the first correspondence indicating a particular structured report path associated with the at least a subset of the one or more elements;

generate a criterion based on the particular structured report path;

based on the particular structured report path, access a node in a DICOM structured report, wherein the DICOM structured report includes a first format that is not queryable;

determine a first value contained in the node;

store the first value in a data structure, wherein the data structure includes a second format that is queryable;

receive a query including one or more filters;

determine second correspondence between the one or more filters and data stored in the data structure; and based on the second correspondence, generate output indicative of at least a subset of the data stored in the data structure.

17. The system of claim 16, further comprising computer-executable instructions to:

determine third correspondence between the particular structured report path and the node of the DICOM structured report, the third correspondence indicating that the DICOM structured report includes the node and the applicability of the criterion to the DICOM structured report.

18. The system of claim 16, further comprising computer-executable instructions to:

receive the user input via the user interface, the user input indicating a rule configured to determine at least one second value based on the first value determined from the DICOM structured report;

determine the at least one second value using the rule; and store the at least one second value in a second data structure, wherein the at least one second value is not included in the DICOM structured report and the output includes an indication of the at least one second value.

19. The system of claim 18, further comprising computer-executable instructions to delete the first value from the data structure subsequent to determining the second value.

20. The system of claim 16, further comprising computer-executable instructions to:

determine correspondence between the one or more filters of a query and the first value; and generate the output to further indicate the first value responsive to the query.

* * * * *